United States Patent
Scarlett et al.

(10) Patent No.: US 9,347,813 B2
(45) Date of Patent: May 24, 2016

(54) CAPACITIVE SENSING PROBE MOTION CONTROL SYSTEM

(71) Applicant: ANALOG DEVICES TECHNOLOGY, Hamilton (BM)

(72) Inventors: James E. Scarlett, Raleigh, NC (US); Thomas G. O'Dwyer, Clonlara (IE); Christopher W. Hyde, Hollis, NH (US)

(73) Assignee: Analog Devices GmbH, Hamilton (BM)

( * ) Notice: Subject to any disclaimer, the term of this patent is extended or adjusted under 35 U.S.C. 154(b) by 310 days.

(21) Appl. No.: 14/165,971

(22) Filed: Jan. 28, 2014

(65) Prior Publication Data

US 2015/0211915 A1   Jul. 30, 2015

(51) Int. Cl.
*G01F 23/26* (2006.01)
*G01N 35/10* (2006.01)

(52) U.S. Cl.
CPC ............ *G01F 23/263* (2013.01); *G01F 23/266* (2013.01); *G01F 23/268* (2013.01); *G01N 35/1011* (2013.01); *G01N 2035/1025* (2013.01)

(58) Field of Classification Search
CPC ... G01F 23/263; G01F 23/266; G01F 23/268; G01N 35/1011; G01N 2035/1025
See application file for complete search history.

(56) References Cited

U.S. PATENT DOCUMENTS

| | | | | |
|---|---|---|---|---|
| 5,270,211 A | * | 12/1993 | Kelln | G01N 35/0092 422/547 |
| 5,866,426 A | * | 2/1999 | Ball | G01F 23/265 340/620 |
| 7,284,427 B2 | * | 10/2007 | Calabrese | G01F 23/268 73/290 R |
| 7,387,023 B2 | * | 6/2008 | Harazin | G01F 23/26 340/620 |
| 8,075,840 B2 | * | 12/2011 | Shimane | G01F 23/265 422/500 |
| 8,418,550 B2 | | 4/2013 | Hampton | |
| 2008/0034847 A1 | | 2/2008 | Golter | |
| 2012/0304732 A1 | | 12/2012 | Marki et al. | |
| 2013/0261539 A1 | | 10/2013 | King | |

FOREIGN PATENT DOCUMENTS

| | | |
|---|---|---|
| EP | 0377508 A1 | 1/1990 |
| EP | 2031409 | 3/2009 |

OTHER PUBLICATIONS

International Search Report for PCT/EP2015-050665 mailed Apr. 10, 2015, 10 pages.
"Level Sensor" extracted from Wikipedia, http://en.wikipedia.org/wiki/Level_sensor, 9 pages, Jan. 14, 2014.
(Continued)

*Primary Examiner* — John Fitzgerald
*Assistant Examiner* — Michael E Turbyfill
(74) *Attorney, Agent, or Firm* — Patent Capital Group

(57) ABSTRACT

Various methods and systems are provided to control a probe moving towards fluid held in a container. The probe is moved towards the fluid to take a sample of the fluid in the container. To take a sample, probe is actuated to hit the fluid surface and to pass the fluid surface by a predetermined distance. Capacitive sensing which incorporates the probe itself is used to support an approach engine for controlling the motion of the probe. The approach engine determines the speed of the probe based on capacitance measurements, and in some cases based on position information of the probe. The approach engine ensures the probe hits the surface of the fluid in the container in order to take a sample while ensuring the probe does not hit the bottom of the container.

20 Claims, 12 Drawing Sheets

(56) References Cited

OTHER PUBLICATIONS

Francis Yee-Hon Wong, "Inductive Position/Velocity Sensor Design and Servo Control of Linear Motor," © 1995 Massachusetts Institute of Technology, Oct. 1, 1994, 136 pages.

Subbarao Lanka and Sachin Gupta, "Use capacitive sensing to Implement reliable liquid level sensing—Part I," EE Times, extracted from the Internet: http://www.eetimes.com/document.asp?doc_id=1279770&print=yes, 4 pages, Jan. 14, 2014.

"RF Capacitance Point Level Sensors—LV800 Series," pp. K41-K42.

Kevin Hambrice and Henry Hopper, "A Dozen Ways to Measure Fluid Level and How They Work," Sensors (Your Technical Resource for Sensing, Communication, and Control), extracted from the Internet: http://www.sensorsmag.com/sensors/leak-level/a-dozen-ways-measure-fluid-level-and-how-they-work-1067, 7 pages, Jan. 14, 2014.

Mark N. Horenstein et al., "Differential capacitive position sensor for planar MEMS structures with vertical motion," Elsevier, Sensors and Actuators 80 (2000) 53-61, www.elsevier.nl/locate/sna, Nov. 16, 1998 and Jul. 12, 1999, 0924-4247/© 2000 Elsevier Science S.A., pp. 53-61.

\* cited by examiner

*BASELINE DATA – EMPTY CUVETTE*

*DISCONTINUITY ONCE PROBE CONTACTS FLUID*

*CAPACITANCE VERSUS DISTANCE (AND FILL LEVEL)*

*NORMALIZED CAPACITANCE VERSUS DISTANCE
(AND FILL LEVEL)*

*SLOPE / CHANGE IN CAPACITANCE VERSUS DISTANCE
(AND FILL LEVEL)*

*READ NUMBER VERSUS CAPACITANCE
APPROACH PLOT*

*PROBE POSITION VERSUS CAPACITANCE*

CAPACITIVE SENSING PROBE MOTION CONTROL SYSTEM

TECHNICAL FIELD OF THE DISCLOSURE

The disclosed technology relates to control systems involving level sensing, and more particularly, to a probe motion control system involving capacitive sensing.

BACKGROUND

Level sensors detect the level of substances that flow, including liquids, slurries, granular materials, and powders. Fluids and fluidized solids flow to become essentially level in their containers (or other physical boundaries) because of gravity whereas most bulk solids pile at an angle of repose to a peak. The substance to be measured can be inside a container. The level measurement can be either continuous or point values. Continuous level sensors measure level within a specified range and determine the exact amount of substance in a certain place, while point-level sensors only indicate whether the substance is above or below the sensing point. Generally the latter detect levels that are excessively high or low.

There are many physical and application variables that affect the selection of the optimal level monitoring method for industrial and commercial processes. The selection criteria can include one or more of the following: phase (liquid, solid or slurry), temperature, pressure or vacuum, chemistry, dielectric constant of medium, density (specific gravity) of medium, agitation (action), acoustical or electrical noise, vibration, mechanical shock, tank or bin size and shape. Also important are the application constraints, which may include: price, accuracy, appearance, response rate, ease of calibration or programming, physical size and mounting of the instrument, monitoring or control of continuous or discrete (point) levels.

Overview

Various methods and systems are provided to control a probe moving towards fluid held in a container. The probe is moved towards the fluid to take a sample of the fluid in the container. To take a sample, probe is actuated to hit the fluid surface and to pass the fluid surface by a predetermined distance. Capacitive sensing which incorporates the probe itself is used to support an approach engine for controlling the motion of the probe. The approach engine determines the speed of the probe based on capacitance measurements, and in some cases based on position information of the probe. The approach engine ensures the probe hits the surface of the fluid in the container in order to take a sample while ensuring the probe does not hit the bottom of the container.

DESCRIPTION OF EXAMPLE EMBODIMENTS OF THE DISCLOSURE

Understanding Capacitive Sensing

Capacitive sensing is a technology based on capacitive coupling. A capacitive sensor can detect characteristics of material(s) nearby a capacitive sensor, such as characteristics of a dielectric mix. The materials may either be conductive and/or have a different dielectric than its surroundings. Capacitive sensing is used in many different types of sensors, including those to detect and measure proximity, position or displacement, humidity, fluid level, and acceleration. Capacitive sensing has become more popular as capacitive sensors for detecting changes in capacitance become more accurate and reliable. For instance, capacitive sensors are used in many devices such as laptop trackpads, digital audio players, computer displays, mobile phones, mobile devices, tablets, etc. Design engineers continue to choose capacitive sensors for their versatility, reliability and robustness, and cost reduction over mechanical switches. The present disclosure focuses on how to use capacitive sensing for controlling a probe moving towards the surface of a fluid in a container, and in some cases, how to determine the level of the fluid in the container.

Capacitive sensing systems typically provide a capacitor in the system comprising of two sufficiently conductive objects, i.e., conductive "plates". In particular, the capacitive sensor can measure the surface charge on one or more of these conductive objects to ascertain the capacitance of the capacitor. The capacitance would provide some indication of the dielectric mix in the capacitor formed between the two conductive objects. One or both of these sufficiently conductive objects may be an electrode (e.g., formed using sufficiently conductive materials), where the electrode is stimulated with an excitation source to generate an electric field. One or both of these sufficiently conductive objects may be read by the capacitive sensor (e.g., through a capacitance to digital converter (CDC)) to determine the amount of surface charge on the sufficiently conductive object, where the surface charge measurement, i.e., the capacitance measurement, provides an indication of capacitance between two "plates" of a capacitor formed by the system.

Figure 1:
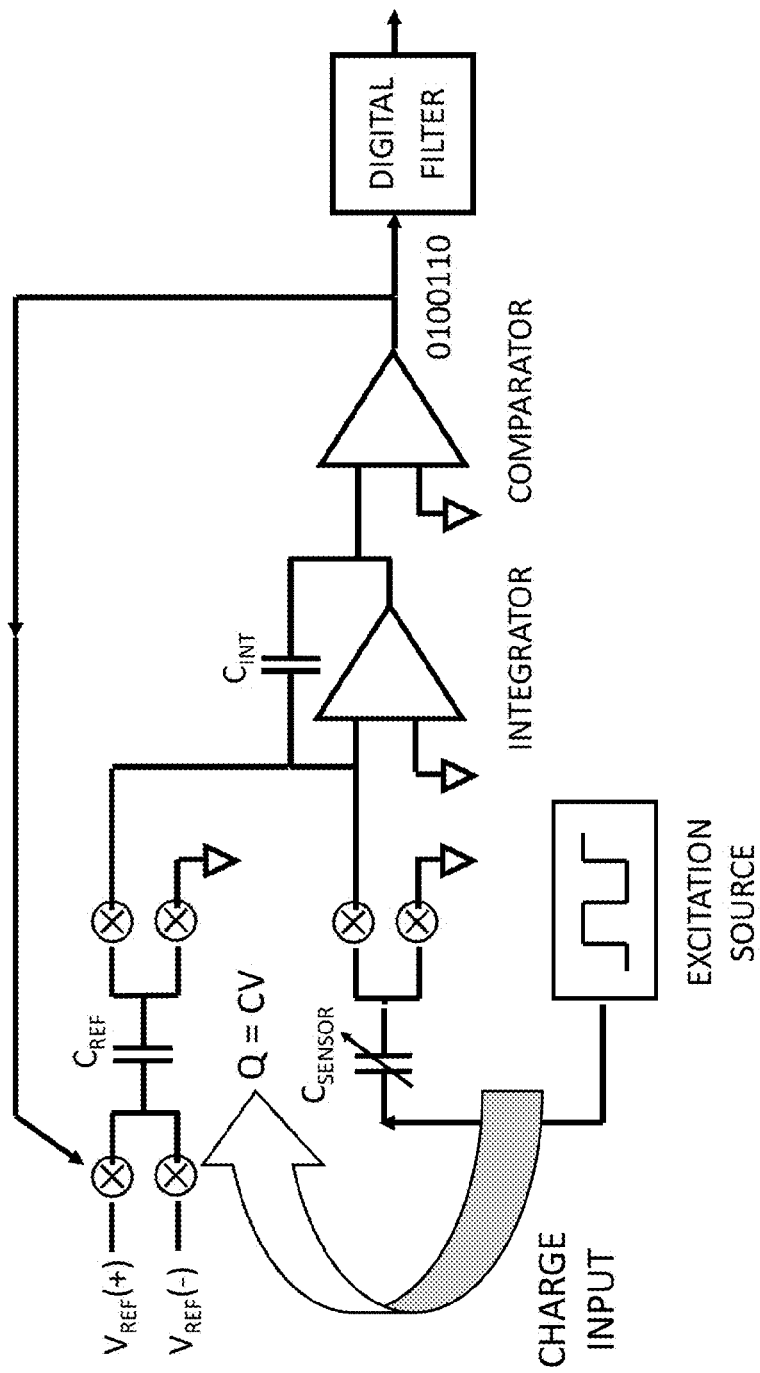
FIG. 1 shows an exemplary implementation of a high resolution capacitance to digital converter (CDC), according to some embodiments of the disclosure.

FIG. 1 shows an exemplary implementation of a high resolution capacitance to digital converter (CDC) for a capacitive sensing system, according to some embodiments of the disclosure. The CDC interfaces with a capacitor $C_{SENSOR}$, i.e., the capacitor having a sensing electrode. One of the plates of the capacitor is connected to an excitation source, which provides a voltage V across the capacitor $C_{SENSOR}$. The voltage V provided by the excitation source (can provide any suitable waveform besides a square wave excitation signal) in turn provides the charge input to the capacitor. The CDC measures the surface charge Q on the sensing electrode. Because Q has a direct relationship with capacitance C and voltage V, the measurement of surface charge thus provides a capacitance measurement. The CDC may continuously sample the charge going through $C_{SENSOR}$.

In some embodiments, the measurement is provided to an integrator, a comparator for quantization, and a digital filter (the combination may depend on the specific implementation of the CDC). Generally, the output provides a digital signal which represents the capacitance measurements taken by the capacitive sensor. The digital signal can then be provided to a processor for further processing.

Different Methods of Level Sensing in a Cuvette or Container

Diagnostic instrumentation must work with fluids in small containers such as test tubes, cuvettes, and reagent bottles. Fluid levels must be known for proper interface between (moving) probes and containers for sample aspiration (i.e., taking a sample just underneath the surface of the fluid). Typically, diagnostic instrumentation may require 1 mm accuracy and less than 0.5 mm resolution. Challenges for these systems include keeping a high speed for the moving probe, environmental sensitivity, consistency, complexity, and cost.

One type of container is a cuvette, which is a small tube of circular or square cross section, sealed at one end, made of plastic, glass, or fused quartz (for UV light) and designed to hold samples for spectroscopic experiments. Disposable plastic cuvettes are often used in fast spectroscopic assays, where speed is more important than high accuracy.

Diagnostic instrumentation may often move a large number of cuvettes while a probe or multiple probes samples each cuvette at a relatively fast speed. A probe typically comprises a hollow tube with a pointed tip for lifting a sample of the fluid through the hollow portion of the tube. The probe allows an accurate amount of sample of the fluid to be lifted/aspirated out of the container. The probe is preferably positioned at or substantially near a prescribed depth below the surface of the fluid to maximize the use of available sample in the container (sample enough but not too much). For this reason, accurate level sensing and control of the probe are important for providing an effective sample aspiration system.

Generally speaking, many mechanisms can be used to measure fluid level. Ultrasonic, radar and laser solutions are possible, but can be very expensive. In-vitro Diagnostic (IVD) systems can employ radio frequency (RF) signals to determine the probe position with respect to the fluid surface. This system is known to be fairly noisy. It is an EMI emitter, which can be a problem. It is also very susceptible to interference from outside electromagnetic radiation.

One implementation of capacitive sensing in level sensing includes placing multiple sensors at discrete levels within or outside a tank to detect discrete levels within the tank (e.g., tank full, tank empty, and other fixed fluid levels). This implementation is practical for containers which are fairly large in size and permanent (not easily disposable), and for applications where low resolution level measurements are tolerable. For an application where cuvettes or similar test sample containers are used, the cuvettes are moved into position one after the other, and it is relatively easy for the probe to be misaligned for a given cuvette or for a capacitive sensor on the side of a cuvette to be misaligned for a given cuvette. Also, while this method can be excellent for determining absolute fill levels, without having precise motor control it is very difficult to determine the probe position relative to the fluid surface.

Another implementation of capacitive sensing in level sensing includes placing two conductive probes (whose length extends from the top of the container to the bottom of the container) in the fluid held by a container to monitor fluid level changes. This implementation is practical if the conductive probes can be maintained stationary in the container and submerged in the fluid during the entirety of the fluid level monitoring operation. Placing such a probe inside the fluid is not practical due to contamination issues in a diagnostic equipment setting. Probes would need to be discarded or cleaned after each test.

Improved Capacitive Sensing in a Control System

One objective of a control system is to move the probe, using a motion control engine, with sufficient speed while having sufficient measurement accuracy of the position of the probe with respect to the surface of the fluid in order to predict upcoming contact with the surface of the fluid in the container. The control system (e.g., including an approach engine) takes capacitance measurements from a capacitive sensor as input using a capacitive-to-digital converter (CDC). Using the capacitance measurements and optionally position information of the probe from a motion control engine, a processor with an approach engine of the control system can transmit signals to the motion control engine (or transmit data for instructing the motion control engine) to appropriately move the probe towards the surface of the fluid in the container, and stopping the probe once the probe hits the surface of the fluid.

Using capacitive sensing is superior over RF level sensing solutions because capacitive sensing does not suffer from EMI susceptibility, as the delta-sigma modulator in the CDC tends to filter this out. The CDC may also filter out interference at power line frequencies.

The Improved Capacitor Being Sensed

In the present disclosure, the capacitor from which the capacitance measurements are made is comprised of two terminals/plates: a conductive plate that sits beneath the container holding a fluid, and the moving probe itself. An excitation signal is applied to one terminal/plate of the capacitor, and the other terminal/plate is connected to the capacitive-to-digital converter (CDC) input. The measured capacitance can be the same regardless of which terminal is connected to the excitation signal or CDC input. The absolute value of this capacitor will depend on the form factors of the plate and the probe, the makeup of the dielectric, distance from the probe to the plate, and other environmental factors. Note that the dielectric includes air, a fluid, and a cuvette for holding the fluid (in the order from the probe to the plate underneath the cuvette). The control system takes advantage of the changing nature of this dielectric mix as the probe approaches the plate.

In its simplest form a capacitor can be described as two parallel plates with a dielectric material between them. The value of capacitance varies with plate size, orientation of one plate versus the other, and dielectric constant, among other factors. By taking advantage of these variables, a capacitive sensor can measure the changing value of an unusual capacitor to determine the probe position relative to the surface of the fluid.

The setup of the capacitor for the capacitive sensor in the control system is unique and nontrivial. The present disclosure utilizes an apparatus where the two "plates" of the capacitor for the capacitive sensor is formed by the moving probe towards the fluid in the container and a conductive plate underneath the container. Such a setup advantageously decreases the complexity of the mechanical system by incorporating the probe itself for the capacitance measurements and providing a relatively non-intrusive conductive plate underneath the probe. Incorporating the probe itself as one plate of the capacitor may also advantageously allow a better measurement to be made which could more directly reflect the relative distance of the probe to the fluid surface.

The moving probe may be highly conductive (e.g., made with metal) or sufficiently conductive (e.g., made with a plastic or composite such that the probe can be disposable). The conductive plate underneath the container may be made with any suitable conductive material. The shape and size of the conductive plate may vary depending on the application. Preferably, the conductive plate matches the size and shape of the bottom of the container.

The Improved Control System

The control system of the present disclosure moves the probe towards the container based on inputs including capacitance measurements from a capacitive sensor (e.g., involving a CDC) and optionally position information of the probe from the motor control engine. The control system may output signals for controlling the motion control engine for moving the probe. In this control system, the capacitance measurements and the position information may be considered as feedback information for adjusting the motion control engine.

Figure 2:
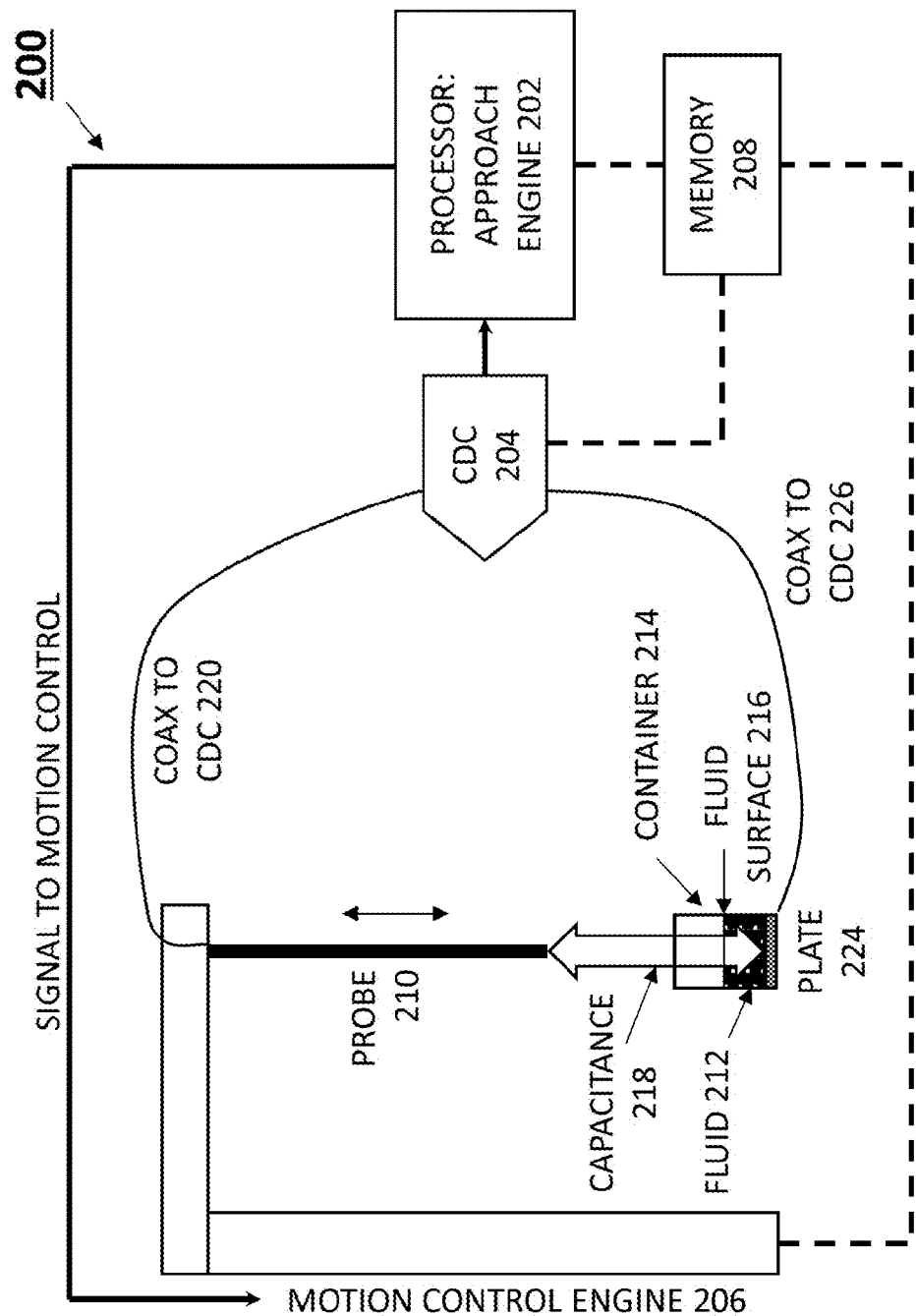
FIG. 2 shows an exemplary configuration utilizing both a high resolution capacitance to digital converter and motion control engine in a control system, according to some embodiments of the disclosure.

FIG. 2 shows an exemplary configuration utilizing both a high resolution capacitance to digital converter and a motion control engine in a control system, according to some embodiments of the disclosure. The control system 200 includes a processor having an approach engine 202 thereon, a capacitive-to-digital converter (CDC) 204, a motion control engine 206, and a memory 208. The control system 200 is configured to control the movement of probe 210 towards (as well as away from) the fluid 212 held in container 214. The fluid 212 may have a fluid surface 216.

The CDC 204 for converting capacitance measurements of the capacitor (i.e., measurements indicative of capacitance 218 between probe 210 and conductive plate 224 underneath the container) into a digital signal may include a modified delta-sigma Analog-to-Digital Converter (ADC). Delta-Sigma ADCs are based on a charge balancing architecture, where there is an unknown input voltage compared to a reference voltage. Each input, unknown and reference, places a charge on identical capacitors to allow the comparison of the two. This structure is changed slightly when the ADC is used as a CDC. In this case, the device provides a known excitation signal, which may be provided either (1) to the probe via coaxial connection 220 to CDC to the probe, or (2) to the conductive plate 224 via coaxial connection 226 to CDC. Since the input is now known, the charge balancing architecture is used to determine the value of an unknown input capacitance compared to the known reference capacitance. In practice, this method can be used to discern capacitance differences on the order of attofarads (aF, or $10^{-18}$ farads).

The approach engine 202 (implemented on one or more processors) is coupled to the output of the CDC 204 and is configured to receive capacitance measurements indicative of the capacitance 218 from CDC 204. The measurements may, in some cases, be stored in memory 208 by the CDC 204 and may be made accessible to approach engine 202 (or may be read by approach engine 202). The approach engine 202 may transmit a signal to the motion control engine 206 to move the probe towards the fluid and/or the container. Transmitting the signal to the motion control engine may include the signal (or data) being stored in memory 208 by the approach engine 202, and the signal being made accessible to motion control engine 206 to adjust the movement of probe 210 (or instruct the probe 210 to move a certain distance and/or at a certain speed).

The motion control engine 206 is configured to move the probe according to a certain distance (e.g., a fixed step) or according to a certain speed (e.g., according to data indicating that distance or speed in memory 208). Position information of the probe and its movement towards the container can be determined and provided by the motion control engine 206. For instance, the position information may be derived from past movements in distance. In another instance, the position information may be derived from a past speed over a period of time. In some instances, for a stepper motor, the position information may be derived by the number of pulses sent to the motor for rotating a certain number of degrees. The angular motion in degrees can be translated to a linear distance and provide the position information of the probe. The motion control engine 206 may write the position information into memory 208, and the position information may be made available to the approach engine 202 for processing. It is noted that position information is not required for proper operation of the control system, but may be used as feedback information to assist or improve the control system. It is further noted that position information provided by a motor control engine provides only an estimate of position of the probe, and may not always be very accurate or precise.

Characterizing the Dielectric Mix

Because the motion control of the probe is based on the capacitance measurements and optionally the position information of the probe relative to the conductive plate, one must first understand the characteristics of the dielectric mix in order to predict when the probe would hit the fluid surface. The characteristic of the dielectric mix is going to differ based on the fluid itself and the container used in the application, as difference in fluid and the container itself may affect the capacitance readings. Furthermore, the capacitance measurements itself will depend on the probe and the conductive plate.

As the probe approaches the plate (in some cases, as the probe position information increases), the capacitance increases. The nature of this change has been observed to be a power series function (quadratic). But the coefficients in this power series change in the presence of a fluid in the probe's path. Since the fluid has a much greater dielectric constant than air, as the fluid becomes a higher percentage of the dielectric between the probe and plate the capacitance increases more rapidly. When the probe approaches very close to the fluid surface, the measured capacitance value accelerates. This can be used to determine proximity to the fluid surface (i.e., relative distance to the fluid surface, or how close the probe is to the fluid surface). Also, if a user can characterize a system with no fluid present, it is possible to normalize the measured data in such a way that it only reflects the dielectric mix, and in particular the impact of the fluid on that mix. It may also be possible to determine the actual level/position of the fluid surface.

Baseline Data: Empty Cuvette

Figure 3:
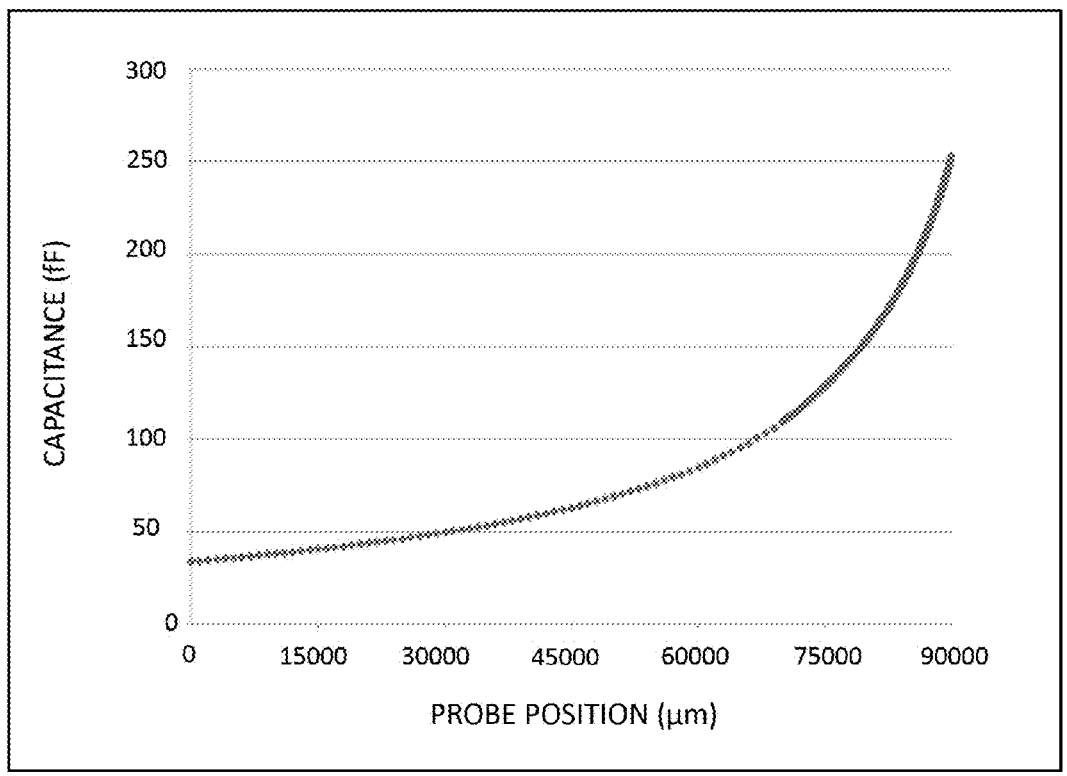
FIG. 3 shows an exemplary plot of probe position versus capacitance (with probe approaching an empty cuvette), according to some embodiments of the disclosure.

FIG. 3 shows an exemplary plot of probe position versus capacitance (with probe approaching an empty cuvette), according to some embodiments of the disclosure. The data shows a probe which is configured to move about 90 mm towards an empty cuvette. 0 mm corresponds to a starting position and 90 mm corresponds to an ending position closer to the empty cuvette and the conductive plate beneath the empty cuvette. The probe position values increases as the probe moves closer towards the empty cuvette and the conductive plate underneath the empty cuvette. As the probe approach the empty container, the capacitance increases as the distance between the probe and the empty cuvette decreases. Generally speaking, capacitance is inversely related to the distance between the two capacitive plates. Accordingly, the data set shown in FIG. 3 shows that the capacitance grows as the probe approaches the empty cuvette (i.e., as probe position information/measurement increases). While not a major contribution, the proportion of the empty cuvette as part of the dielectric mix increases as the probe approaches towards the empty cuvette and contributes slightly to the increase in capacitance. Moreover, the data shows an increase in slope as the probe gets closer and closer to the empty cuvette. This baseline data can be used for normalizing capacitance measurements, if position information is known, in a setup where the cuvette is non-empty to remove the effect of the cuvette on the capacitance measurement.

Power Series Model and Discontinuity: Non-Empty Cuvette

Figure 4:
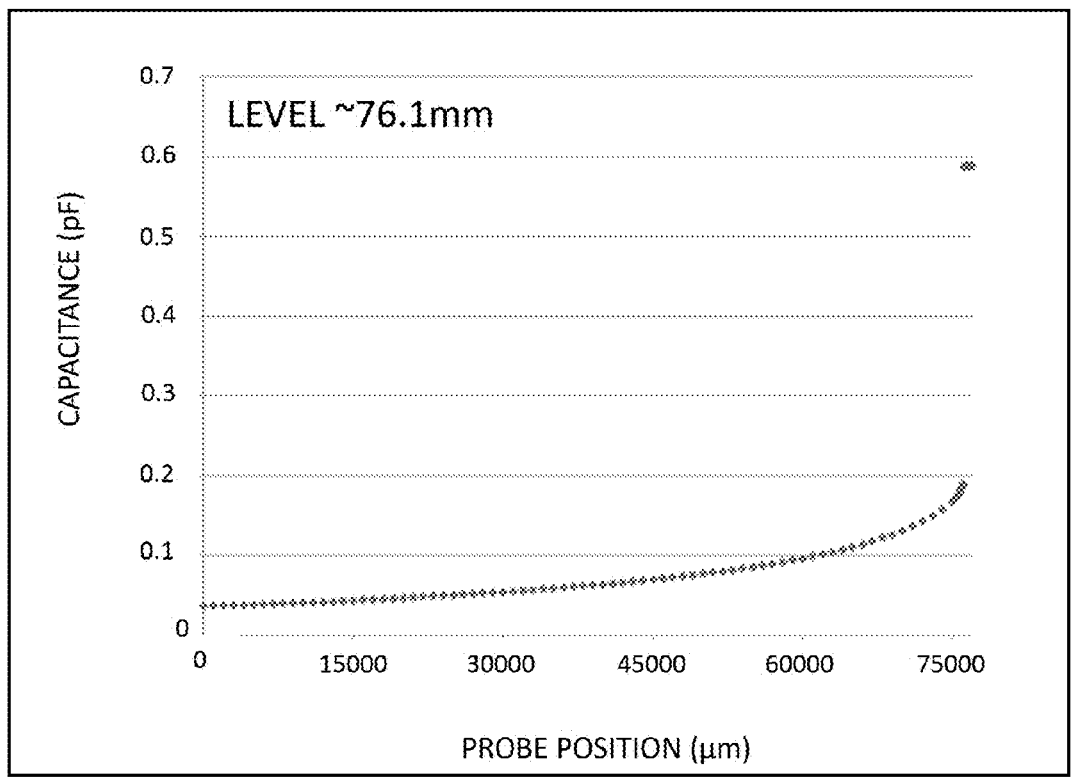
FIG. 4 shows an exemplary plot of probe position versus capacitance (with probe approaching a non-empty cuvette), according to some embodiments of the disclosure.

FIG. 4 shows an exemplary plot of probe position versus capacitance (with probe approaching a non-empty cuvette as probe position values increase), according to some embodiments of the disclosure. In this example, the cuvette holds fluid therein and the fluid level is approximately measured at 76.1 mm in terms of the position information of the probe. From the plot, a characteristic can be noted with respect to the fluid/probe relationship. Once the probe has made contact with the fluid, there is a discontinuity in the capacitance curve. The measured value after the large jump appears to be a multiple of the value measured just prior to contact being made. It is further noted that the measured value changes very little as the probe is moved through the fluid. The discontinuity is so large that a predetermined capacitance threshold (or some other suitable trigger criteria) can be used for checking for the discontinuity (indicating that the probe has hit the fluid surface, or that the probe is likely to have touched the surface of the fluid in the container). Since an objective of this control system is to insert the probe a known, small distance into the fluid, this behavior is an important one to the control system, as it can be used to determine when the probe should stop moving towards the conductive plate underneath the cuvette.

Example

Capacitance Values for Three Different Fluid Levels

Figure 5:
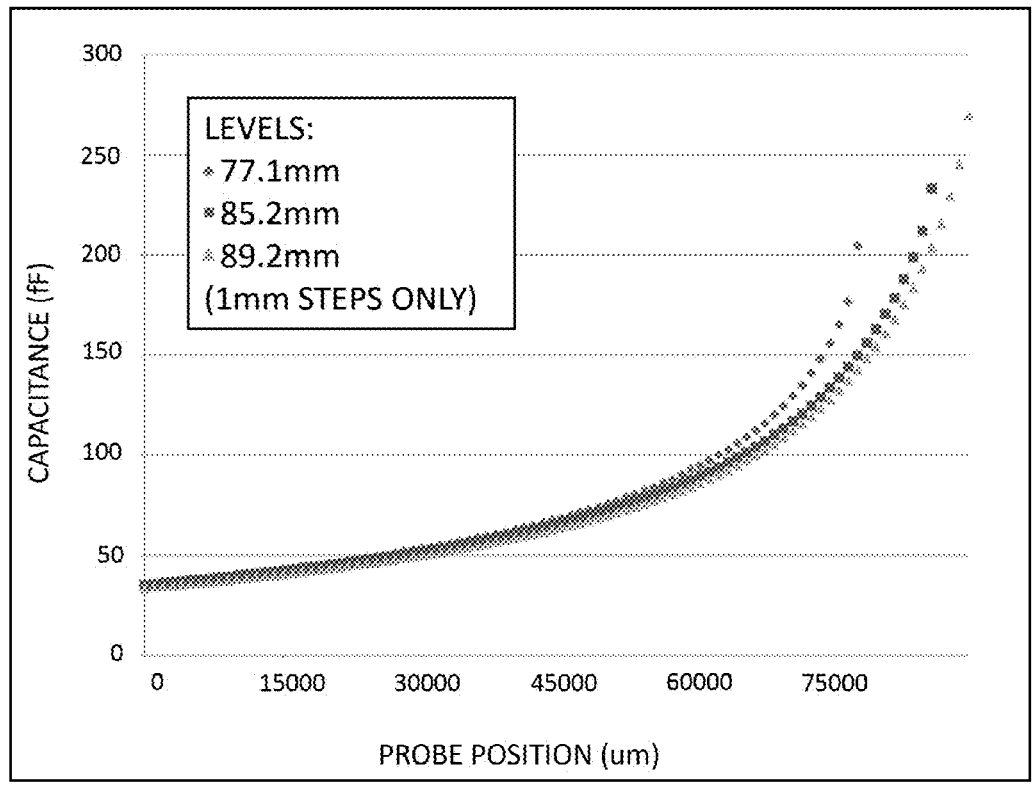
FIG. 5 shows an exemplary plot of distance between probe and plate versus capacitance (for three different series of data corresponding to three probes each approaching a non-empty cuvette at three different fluid levels), according to some embodiments of the disclosure.

FIG. 5 shows an exemplary plot of distance between probe and plate versus capacitance (for three different series of data corresponding to three probes each approaching a non-empty cuvette at three different fluid levels), according to some embodiments of the disclosure. As the distance between the probe and the conductive plate decreases (i.e., as probe position information values increases), the capacitance increases, as observed in the plot as well of FIG. 4. This plot showing three series of data illustrates the difference in capacitance with respect to the fluid level. Known data at various fluid levels and probe position information may be used to determine the exact fluid level according to the spread exhibited by the known data. It can be shown that at the same distance between the probe and the conductive plate, the capacitance is the highest for a fuller cuvette (e.g., having a fluid level at 77.1 mm), the capacitance is lower for a less full cuvette (e.g., having a fluid level at 85.2 mm), and the capacitance is the lowest for an even less filled cuvette (e.g., having a fluid level at 89.2 mm).

Example

Normalized Capacitance Values for Three Different Fluid Levels

Figure 6:
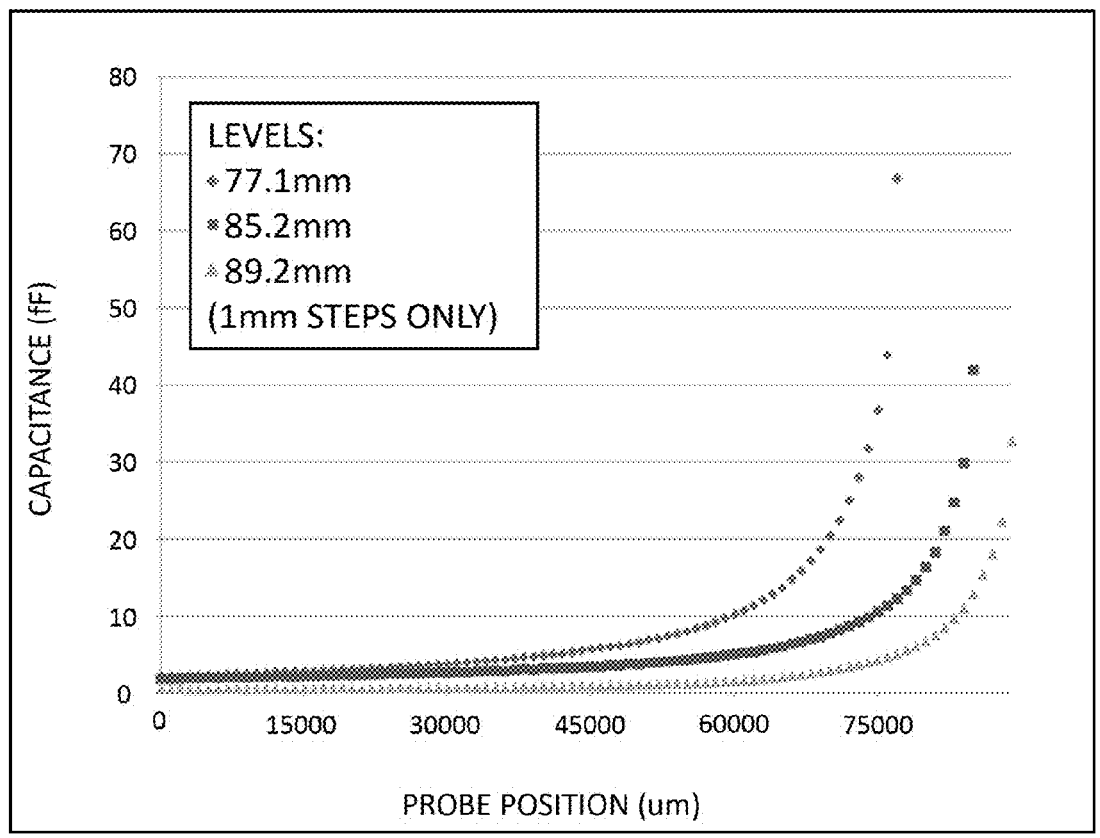
FIG. 6 shows an exemplary plot of distance between probe and plate versus capacitance normalized based on data from an empty cuvette (for three different series of data corresponding to three probes each approaching a non-empty cuvette at three different fluid levels), according to some embodiments of the disclosure.

FIG. 6 shows an exemplary plot of distance between probe and plate versus capacitance normalized based on data from an empty cuvette (for three different series of data corresponding to three probes each approaching a non-empty cuvette at three different fluid levels), according to some embodiments of the disclosure. Normalization within the context of this disclosure may include subtracting or dividing the measured/raw capacitance value based on a corresponding capacitance value observed with an empty cuvette having the same probe position information. By normalizing the data, a difference or spread is observed whereby the normalized capacitance value is notably smaller for lower fluid levels. As shown in the plot, the normalized capacitance measurement values highest for fluid level at 77.1 mm (fuller), lower for fluid level at 85.2 mm (less full), and lowest for fluid level at 89.2 mm (least full). This can be useful for determining whether the fluid surface is very close to the bottom of the cuvette, and therefore care must be taken to not drive the probe through the bottom. As seen in FIG. 6, the spread between the curves are apparent (more apparent than the raw data shown in FIG. 5), and thus can be used as known data at various fluid levels and probe position information to determine the exact fluid level according to the spread. It is further noted that the slope of the curves is also greater for the normalized data than the slope of the raw data. The more drastic change in slope may be more useful/beneficial for setting a threshold on the slope or the estimated slope of change in capacitance versus the change in position.

Example

Figure 7:
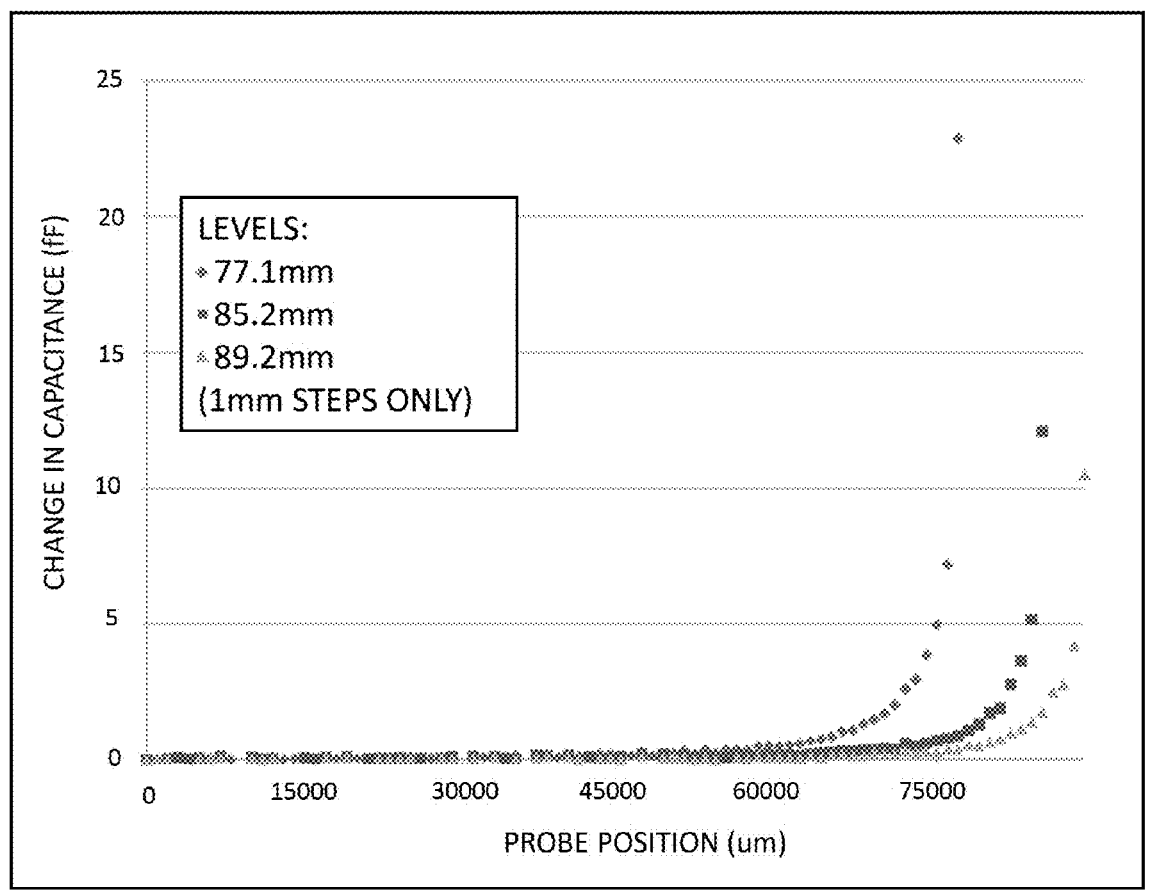
FIG. 7 shows an exemplary plot of distance between probe and plate versus change in capacitance of the normalized data sets shown in FIG. 6 (for three different series of data corresponding to three probes each approaching a non-empty cuvette at three different fluid levels), according to some embodiments of the disclosure.

Slope of Capacitance Values with Respect to Probe Position for Three Different Fluid Levels FIG. 7 shows an exemplary plot of distance between probe and plate versus change in capacitance of the normalized data sets shown in FIG. 6 (for three different series of data corresponding to three probes each approaching a non-empty cuvette at three different fluid levels), according to some embodiments of the disclosure. Besides using raw values of capacitance measurements, the control system can in addition or alternatively take advantage of the increase in slope, i.e., change in capacitance over change in probe position, to control the motion of the probe towards the fluid. Slope allows the control system to predict how close the probe is to the fluid surface and to detect the discontinuity in the capacitance to detect whether the probe has hit the fluid surface. As seen in the plot, a predetermined slope threshold (or some other suitable trigger criteria) can be used to determine whether the probe is reaching close to the fluid surface in the container.

Slope can be determined (or estimated) in different ways. The slope can be determined by dividing the change in capacitance by the change in position information. However, position information is not always available. Thus, the slope can be estimated, during operation, based simply on the change in capacitance between consecutive reads on capacitance measurements (which are made very quickly, at regular/periodic intervals, while the probe is moving at more or less the same distance between reads), or nearby capacitance reads made within a very short time interval (e.g., within milliseconds while the probe is moving). One exemplary system may obtain capacitance measurements as fast as 83 Hz with a very short time interval in between reads while the probe is moving a substantially constant speed at the time when the capacitive reads are made. The measurements in one exemplary system may have an interval of 50 ms or more, while for another exemplary system the interval may be 5 ms or less as the probe is moving at a substantially constant speed.

Example

Approach Plot

Figure 8:
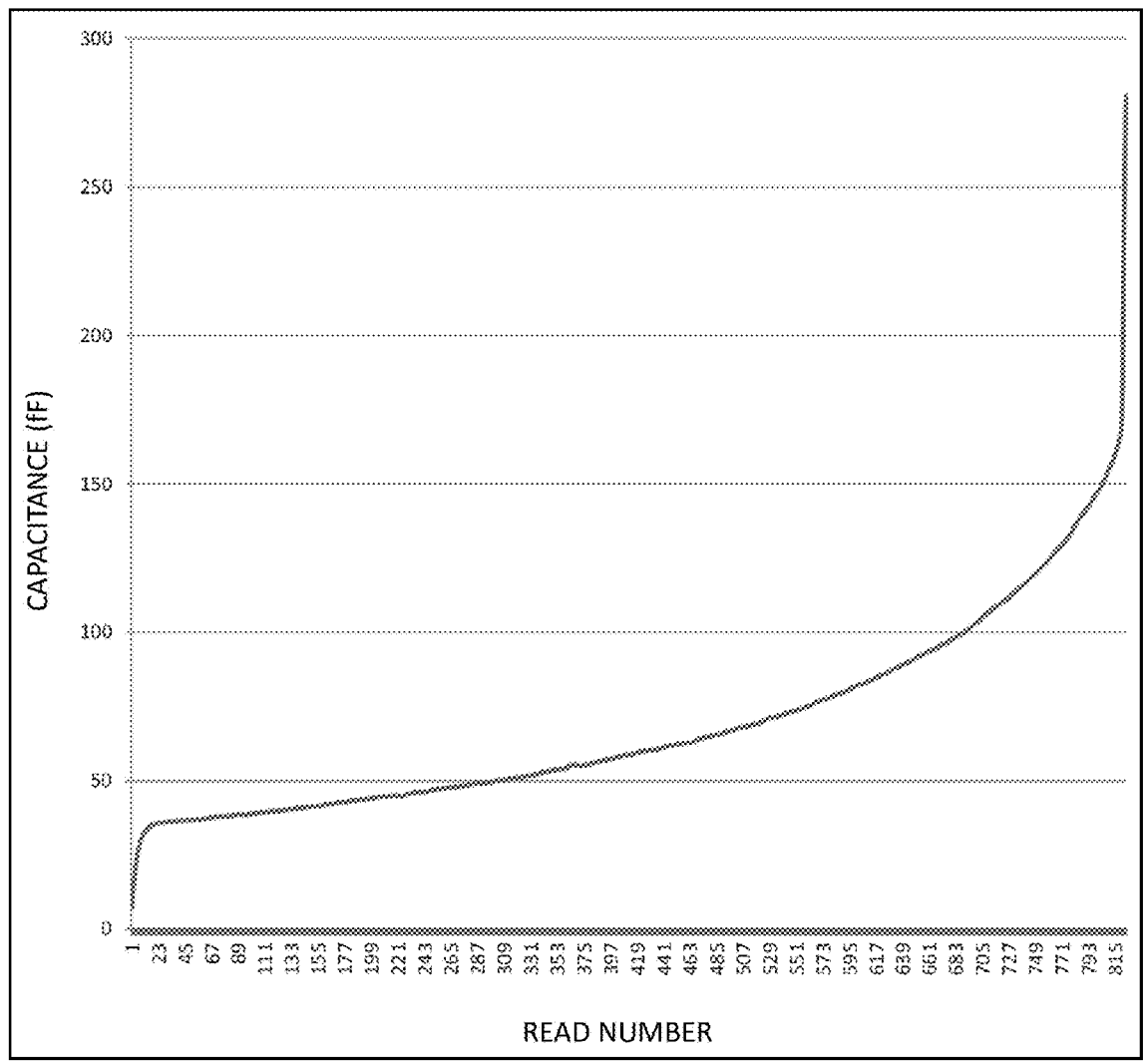
FIG. 8 shows an exemplary approach plot of read number versus capacitance, according to some embodiments of the disclosure.

FIG. 8 shows an exemplary approach plot of read number versus capacitance, according to some embodiments of the disclosure. This approach plot illustrates the behavior of capacitance at different reads at periodic intervals (how fast the probe is moving towards the container is not shown, however). The approach profile shown illustrates data which has been filtered using a modified exponential moving average. Any type of suitable filter, e.g., other moving average filters, or smoothing functions, can be used for filtering the data during operation to filter out noise in the capacitance measurements. The first set of reads (e.g., 1-23) show a quick rise in capacitance, which is an artifact of the moving average catching up in the beginning, and not a result of a steep increase in actual raw capacitance measurements. The last set of reads of filtered data show almost a vertical line (e.g., 793 onwards), a steep increase in capacitance, which represents an actual jump in the raw capacitance measurements.

Example

Level Determination Based on Capacitive Readings

Figure 9:
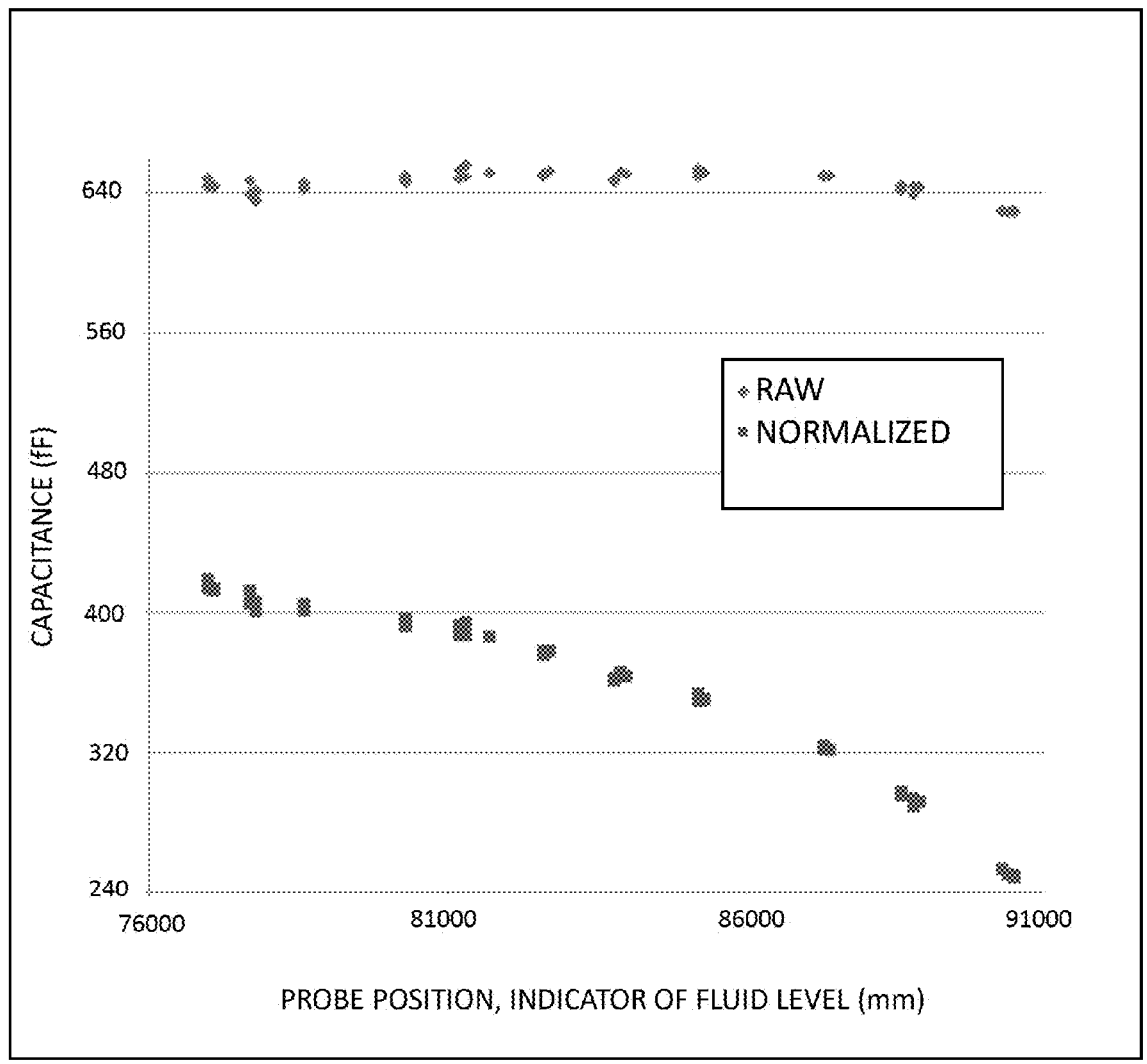
FIG. 9 shows an exemplary plot of probe position upon meeting the fluid surface versus capacitance, according to some embodiments of the disclosure.

FIG. 9 shows an exemplary plot of probe position upon meeting the fluid surface versus capacitance, according to some embodiments of the disclosure. This plot illustrates that the capacitance measurement when the control system detects the probe has hit the fluid surface, when normalized, can be used to deduce the fluid level (illustrating the spread that can be seen in FIG. 7). Instead of simply detecting that the probe is close to the fluid level, the absolute height of the fluid level can be determined using this plot of normalized data. This enables the control system to detect when the fluid level becomes too low for further samples to be taken and avoid driving the probe too close to the bottom of the cuvette if aspiration is to be repeated for the cuvette. Alternatively, position information (if available) can be used as a separate or additional check to stop the probe if the position hits a predetermined position threshold to avoid driving the probe too close to the bottom of the cuvette.

Approach Method

Figure 10:
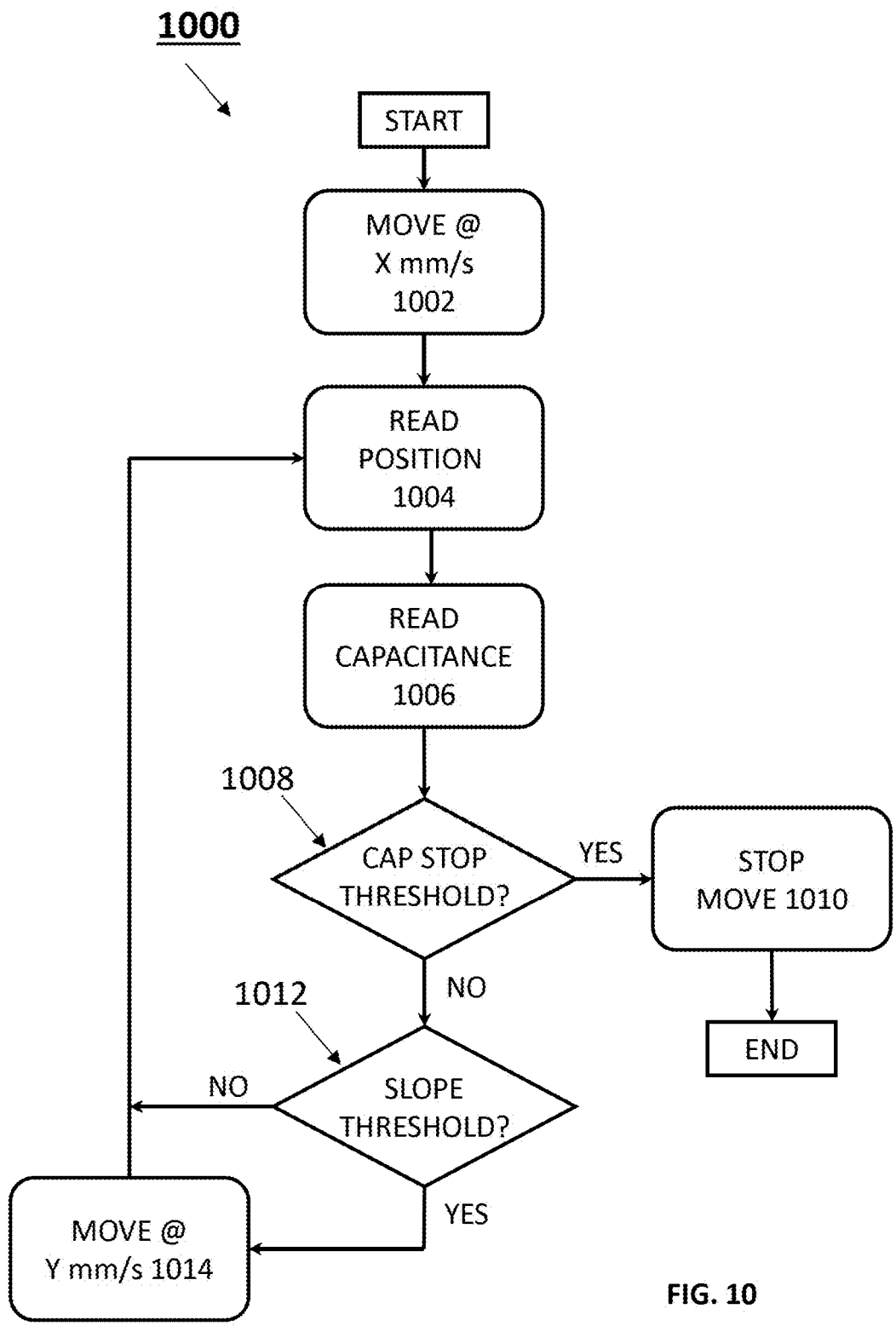
FIG. 10 shows an exemplary flow diagram of a method usable by a control system moving a probe towards a container, according to some embodiments of the disclosure.

FIG. 10 shows an exemplary flow diagram of a method usable by a control system moving a probe towards a container, according to some embodiments of the disclosure. The exemplary method 1000 provides a mechanism for moving the probe towards the surface of the fluid in the container while taking capacitance measurements and optionally position information into account. This method allows the probe to move as quickly as possible towards the fluid surface, but slows down the probe when the probe gets close to the fluid surface. The method also stops the probe once it has hit the fluid surface, or reached a predetermined distance beneath the fluid surface.

The method for controlling movement of the probe towards a container having fluid therein is illustrated in this figure. The probe may already be moving at a first speed, e.g., at X millimeter per second) (box 1002). The approach engine may (optionally) receive from the motor control engine position information (box 1004), and receive from the capacitance-to-digital converter (CDC) capacitance measurement(s) (box 1006). The order of these steps may differ. It is possible, depending on data bandwidth, position information is not available while capacitance measurements are available, or capacitance measurements are not available while position information is available.

The approach engine may check whether the capacitance measurement exceeds a predetermined capacitance threshold (check 1008). If the capacitance measurement exceeds (or meets or exceeds) the predetermined capacitance threshold, it is determined that the probe is likely to have hit the fluid surface. Accordingly, the approach engine would cause the probe to stop moving (box 1010). This would allow the probe to stop very quickly after surface penetration (e.g., as little as 0.05-0.25 mm underneath the surface depending on system configuration parameters). If the capacitance measurement has not exceeded the predetermined capacitance threshold, the method continues.

The approach engine may check whether the slope of the capacitance measurements with respect to position information exceeds (or meets or exceeds) a predetermined slope threshold, which may indicate that the probe is reaching close to the surface of the fluid in the container (e.g., 5-10 mm away from the fluid surface, or even less, such as 1-2 mm away from the fluid surface, depending on the accuracy and speed of measurements). If the slope of the capacitance measurements with respect to position information does exceed the predetermined slope threshold, the approach engine causes the probe to slow down by moving the slope at a second speed (e.g., Y mm/s) (box 1014). If the slope of the capacitance measurements with respect to position information does not exceed the predetermined threshold, the method continues, and, e.g., loops back to box 1004.

To illustrate the method, the following passages describe an exemplary method for controlling movement of a probe towards a container having fluid therein. The method comprises receiving a first capacitance measurement at an approach engine from a capacitive sensor, wherein the first capacitance measurement is indicative of capacitance between the probe and a conductive plate underneath the container. Advantageously, the approach engine can deduce how close the probe is to the fluid surface from the capacitance measurement. Based on the capacitance measurement, the approach engine can determine a first speed appropriate for moving the probe, and the approach engine can transmit a first signal to the motion control engine for moving the probe towards the container at a first speed. For instance, depending on the capacitance measurement, the approach engine may speed up or slow down the probe in its approach towards the fluid in the container.

The method may in some embodiments further include receiving a first position information from a motion control engine, wherein the first position measurement is indicative of the position of the probe relative to the conductive plate. The first speed can be determined based further on the first position information. For instance, the position information can be used in normalization, slope determination for slowing down the probe and/or level determination to prevent the probe from going too far into the cuvette at the next sample aspiration.

The method may in some embodiments further include the first speed being zero to stop the movement of the probe towards the container if the first capacitance measurement exceeds a predetermined capacitance threshold. This allows the approach engine to stop the movement of the probe once a large discontinuity in the capacitance measurements is detected, because the predetermined capacitance threshold indicates that the probe is likely to have hit the surface of the fluid in the container.

The method may in some embodiments, further include the approach engine receiving a second capacitance measurement and a third capacitance measurement from the capacitive sensor. The second capacitance measurement and the third capacitance measurement are each indicative of the capacitance formed between the probe and a conductive plate underneath the container. The capacitance measurements (i.e., capacitance measurements of consecutive reads or capacitance measurements made within a short time interval) enable a slope of the capacitance measurements with respect to position information to be estimated (even if position information is not available). To determine the slope, the approach engine determines (or computes) a change in capacitance between the second capacitance measurement and the third capacitance measurement. Based on the change in capacitance between reads, the slope can be estimated.

In some embodiments, the approach engine receives a second position information and a third position information from a motion control engine, wherein the second position information and the third position information are each indicative of the position of the probe relative to the conductive plate. The second and third capacitance measurements and the position information enable a slope of the capacitance measurements with respect to position information to be determined (rather than estimated from only the capacitance measurements). To determine the slope, the approach engine determines (or computes) a change in capacitance between the second capacitance measurement and the third capacitance measurement and determines a change in position between the second position information and the third position information. Based on the two changes, a slope can be determined.

The slope can affect the speed at which the probe should move. Accordingly the approach engine can transmit a second signal to the motion control engine for moving the probe towards the container at a second speed, wherein the second speed is determined based on the slope (or estimated slope). If the slope (or estimated slope) exceeds a predetermined slope threshold, the second speed is set to be slower than the first speed in order to slow the movement of the probe. This condition likely indicates that the probe is reaching close to the surface of the fluid in the container.

Figure 11:
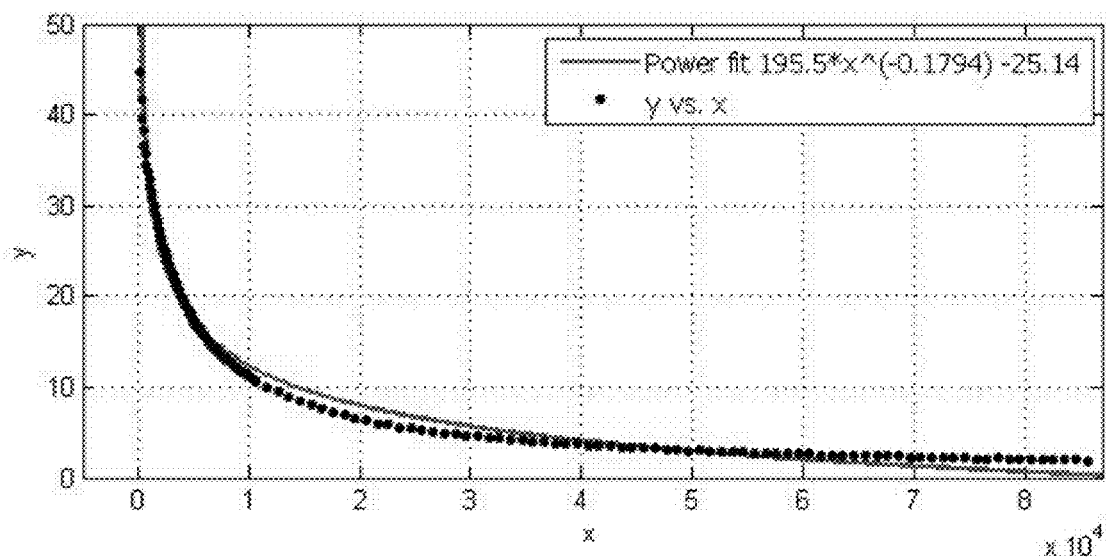
FIG. 11 shows an exemplary power series function estimate of position information versus capacitance measurements, according to some embodiments of the disclosure.

The capacitive sensor, in some cases working with or in a capacitance-to-digital converter, is configured to measure the capacitance between the probe and the conductive plate having a dielectric mix comprising air, the fluid in the container, and the container (in this order from the probe to the conductive plate). If baseline measurements are available (e.g., such as data shown in FIG. 3), the baseline data can be used to provide a model of the container's contribution to the capacitance. FIG. 12 shows an exemplary power fit estimate of position information versus capacitance measurements, according to some embodiments of the disclosure. Using the model, the first capacitance measurement, the second capacitance measurement, and/or the third capacitance measurement can be normalized based on a power series function representative of measurement data comprising position information versus capacitance measurements obtained from moving the probe towards the empty container. An illustrative power series fit of baseline capacitance measurements (e.g., a reversed×power fit) is shown in FIG. 11, which may be used for interpolating a baseline capacitance measurement based on observed position information. Advantageously, the change in slope of normalized capacitance measurement as the probe moves closer to the fluid surface is more pronounced than the change in slope of raw capacitance measurement. This allows the system to have a more robust predetermined slope threshold (or some other trigger criteria) for accurately determining or ascertaining when the probe is very close to the surface of the fluid.

Configuring the Terminals, Ground, and Excitation Source

Figure 12A:
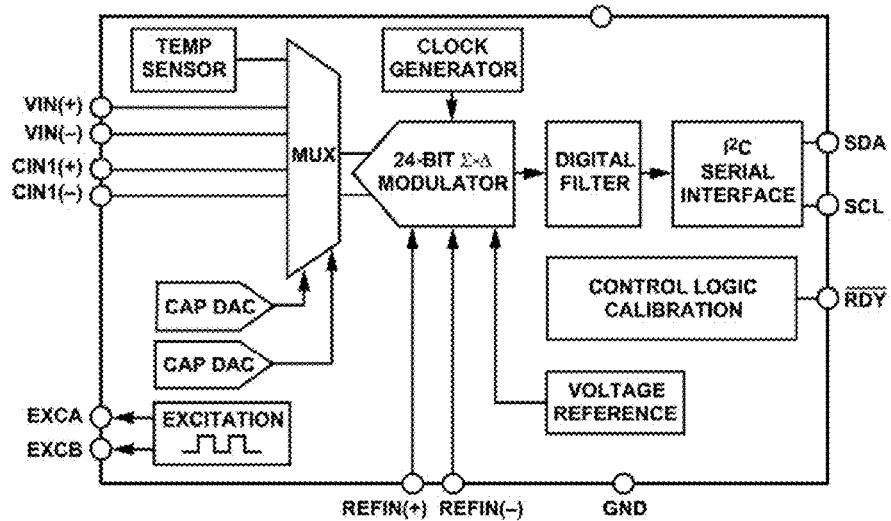
FIGS. 12A-B shows two exemplary capacitance to digital converters usable with the control system to measure capacitance, according to some embodiments of the disclosure.
Figure 12B:
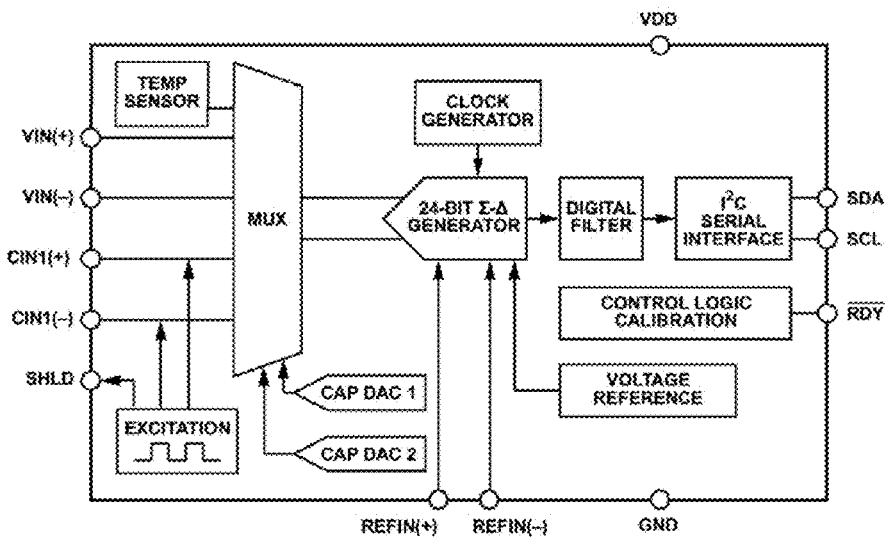

FIGS. 12A-B shows two exemplary capacitance to digital converters (CDCs) usable with the control system to measure capacitance, according to some embodiments of the disclosure. In FIG. 12A, the system shown corresponds to an illustrative block diagram of a CDC which uses floating capacitive sensors where both terminals/plates of the capacitor being sensed are isolated from ground. In FIG. 12B, the system shown corresponds to an illustrative block diagram of a CDC which uses single-ended or differential capacitive sensors where one terminal/plate of the capacitor being sensed is connected to ground.

It is noted that the methods and systems disclosed herein are usable with both types of CDCs. The choice of which terminal/plate to excite and which terminal/plate to read from (i.e., the probe or the conductive plate beneath the container) may depend on the application. Generally speaking, the floating dual ended capacitive sensor may be more sensitive (can obtain better capacitance measurements) than single-ended capacitive sensors. For complexity reasons, if a simpler design is desired, the application may use the single-ended capacitive sensors instead (e.g., to avoid having signal connectivity to both the probe and the conductive plate).

In one embodiment, the capacitive sensor (the CDC) is configured to take the first capacitance measurement by providing an excitation source to the probe and reading the first capacitance measurement from the conductive plate. In another embodiment, the capacitive sensor (the CDC) is configured to take the first capacitance measurement by providing an excitation source to the conductive plate and reading the first capacitance measurement from the conductive plate. These embodiments can be implemented using the illustrative system shown in FIG. 12A.

In one embodiment, the capacitive sensor (the CDC) is configured to take the first capacitance measurement by grounding the conductive plate, providing an excitation source to the probe and reading the first capacitance measurement from the probe. Alternatively, the capacitive sensor (the CDC) is configured to take the first capacitance measurement by grounding the probe, providing an excitation source to the conductive plate and reading the first capacitance measurement from the conductive plate. These embodiments can be implemented using the illustrative system shown in FIG. 12B.

Variations of the Systems and Methods

In the discussions of the embodiments above, the capacitors, clocks, DFFs, dividers, inductors, resistors, amplifiers, switches, digital core, transistors, and/or other components can readily be replaced, substituted, or otherwise modified in order to accommodate particular circuitry needs. Moreover, it should be noted that the use of complementary electronic devices, hardware, software, etc. offer an equally viable option for implementing the teachings of the present disclosure.

In one example embodiment, any number of electrical circuits and components for providing the system for controlling movement of a probe towards a container of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself.

In another example embodiment, the electrical circuits and components of the FIGURES may be implemented as stand-alone modules (e.g., a device with associated components and circuitry configured to perform a specific application or function) or implemented as plug-in modules into application specific hardware of electronic devices. Note that particular embodiments of the present disclosure may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the amplification functionalities may be implemented in one or more silicon cores in Application Specific Integrated Circuits (ASICs), Field Programmable Gate Arrays (FPGAs), and other semiconductor chips.

It is also imperative to note that all of the specifications, dimensions, and relationships outlined herein (e.g., the number of processors, logic operations, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, example embodiments have been described with reference to particular processor and/or component arrangements. Various modifications and changes may be made to such embodiments without departing from the scope of the appended claims. The description and drawings are, accordingly, to be regarded in an illustrative rather than in a restrictive sense.

In certain contexts, the features discussed herein can be applicable to medical systems, scientific instrumentation, food processing, chemical processing, and any application where the control of motion of a probe-like object towards a fluid surface is desired. In yet other example scenarios, the teachings of the present disclosure can be applicable in the industrial markets that include process control systems involving motion control of a probe a fluid surface that help drive productivity, efficiency, and reliability.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

Other Notes, Examples, and Implementations

Note that all optional features of the apparatus described above may also be implemented with respect to the method or process described herein and specifics in the examples may be used anywhere in one or more embodiments.

In a first example, a control system is provided (that can include any suitable circuitry, dividers, capacitors, resistors, inductors, ADCs, DFFs, logic gates, software, hardware, links, etc.) that can be part of any type of computer, which can further include a circuit board coupled to a plurality of electronic components. The system can include means for clocking data from the digital core onto a first data output of a macro using a first clock, the first clock being a macro clock; means for clocking the data from the first data output of the macro into the physical interface using a second clock, the second clock being a physical interface clock; means for clocking a first reset signal from the digital core onto a reset output of the macro using the macro clock, the first reset signal output used as a second reset signal; means for sampling the second reset signal using a third clock, which provides a clock rate greater than the rate of the second clock, to generate a sampled reset signal; and means for resetting the second clock to a predetermined state in the physical interface in response to a transition of the sampled reset signal.

The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes non-transitory computer-readable memory that further comprises machine-readable instructions that when executed cause the system to perform any of the activities discussed above.

What is claimed is:

1. A method for controlling movement of a probe towards a container having fluid therein, the method comprising:
    receiving a first capacitance measurement from a capacitive sensor, wherein the first capacitance measurement is indicative of capacitance between the probe and a conductive plate underneath the container; and
    transmitting a first signal to the motion control engine for moving the probe towards the container at a first speed, wherein the first speed is determined based on the first capacitance measurement.

2. The method according to claim 1, further comprising:
    receiving a first position information from a motion control engine, wherein the first position information is indicative of the position of the probe relative to the conductive plate; and
    wherein the first speed is determined based further on the first position information.

3. The method according to claim 1, wherein the first speed is zero to stop the movement of the probe towards the container if the first capacitance measurement exceeds a predetermined capacitance threshold.

4. The method according to claim 1, wherein the predetermined capacitance threshold indicates that the probe is likely to have hit the surface of the fluid in the container.

5. The method of claim 1, further comprising:
    receiving a second capacitance measurement and a third capacitance measurement from the capacitive sensor, wherein the second capacitance measurement and the third capacitance measurement are each indicative of the capacitance formed between the probe and a conductive plate underneath the container;
    determining a change in capacitance between the second capacitance measurement and the third capacitance measurement to estimate a slope indicative of change in capacitance with respect to change in position information; and
    transmitting a second signal to the motion control engine for moving the probe towards the container at a second speed, wherein the second speed is determined based on the change in capacitance.

6. The method of claim 1, wherein the capacitive sensor is configured to take the first capacitance measurement by providing an excitation source to the conductive plate and reading the first capacitance measurement from the conductive plate.

7. The method of claim 1, wherein the capacitive sensor is configured to take the first capacitance measurement by grounding the conductive plate, providing an excitation source to the probe and reading the first capacitance measurement from the probe.

8. The method of claim 5, wherein the second capacitance measurement and the third capacitance measurement are normalized based on a power series function representative of measurement data comprising position information versus capacitance measurements obtained from moving the probe towards the empty container.

9. The method of claim 5, wherein the second speed is less than the first speed if the change in capacitance exceeds a predetermined slope threshold to slow the movement of the probe.

10. The method of claim 1, wherein the capacitive sensor is configured to take the first capacitance measurement by providing an excitation source to the probe and reading the first capacitance measurement from the conductive plate.

11. The method of claim 9, wherein the predetermined slope threshold indicates that the probe is reaching close to the surface of the fluid in the container.

12. The method of claim 1, wherein the capacitive sensor is configured to measure the capacitance between the probe and the conductive plate having a dielectric mix comprising air, the fluid in the container, and the container.

13. The method of claim 1, wherein the first capacitance measurement is normalized based on a power series function representative of measurement data comprising position information versus capacitance measurements obtained from moving the probe towards the empty container.

14. A system for controlling movement of a probe towards a container having fluid therein, the system comprising:
    a capacitive to digital converter for converting measurements from a capacitive sensor into a digital signal;
    a motion control engine for moving the probe towards the container;
    an approach engine coupled to the output of the capacitive to digital converter configured to:
        receive a first capacitance measurement from the capacitive sensor, wherein the first capacitance measurement is indicative of capacitance between the probe and a conductive plate underneath the container; and
        transmit a first signal to the motion control engine for moving the probe towards the container at a first speed, wherein the first speed is determined based on the first capacitance measurement.

15. The system according to claim 14, wherein the first speed is zero to stop the movement of the probe towards the container if the first capacitance measurement exceeds a predetermined capacitance threshold.

16. The system of claim 14, wherein the approach engine is further configured to:
    receive a second capacitance measurement and a third capacitance measurement from the capacitive sensor, wherein the second capacitance measurement and the third capacitance measurement are each indicative of the capacitance formed between the probe and a conductive plate underneath the container;
    determine a change in capacitance between the second capacitance measurement and the third capacitance measurement to estimate a slope indicative of change in capacitance with respect to change in position information; and transmit a second signal to the motion control engine for moving the probe towards the container at a second speed, wherein the second speed is determined based on the change in capacitance.

17. The system of claim 14, wherein the first capacitance measurement is normalized based on a power series function representative of measurement data comprising position information versus capacitance measurements obtained from moving the probe towards the empty container.

18. A non-transitory computer readable storage medium having instructions stored thereon for controlling movement of a probe towards a container having fluid therein, wherein the instructions when executed by at least one processor cause the at least one processor to perform the following operations:
   receiving a first capacitance measurement from a capacitive sensor, wherein the first capacitance measurement is indicative of capacitance between the probe and a conductive plate underneath the container; and
   transmitting a first signal to the motion control engine for moving the probe towards the container at a first speed, wherein the first speed is determined based on the first capacitance measurement.

19. The medium according to claim 18, wherein the first speed is zero to stop the movement of the probe towards the container if the first capacitance measurement exceeds a predetermined capacitance threshold.

20. The medium of claim 18, wherein the at least one processor is further configured to perform the following operations:
   receive a second capacitance measurement and a third capacitance measurement from the capacitive sensor, wherein the second capacitance measurement and the third capacitance measurement are each indicative of the capacitance formed between the probe and a conductive plate underneath the container;
   determine a change in capacitance between the second capacitance measurement and the third capacitance measurement to estimate a slope indicative of change in capacitance with respect to change in position information; and
   transmit a second signal to the motion control engine for moving the probe towards the container at a second speed, wherein the second speed is determined based on the change in capacitance.

* * * * *